United States Patent [19]

Revici

[11] Patent Number: 4,564,634
[45] Date of Patent: Jan. 14, 1986

[54] SELENIUM COMPOUNDS HAVING ANTINEOPLASTIC ACTIVITY, PROCESS FOR THE PREPARATION THEREOF AND PHARMACEUTICAL COMPOSITIONS THEREFROM

[75] Inventor: Emanuel Revici, New York, N.Y.

[73] Assignee: Alphatime Ltd. Co., Inc., St. Treviglio, Italy

[21] Appl. No.: 496,111

[22] Filed: May 19, 1983

[30] Foreign Application Priority Data

May 28, 1982 [IT] Italy ............................... 21552 A/82
Apr. 19, 1983 [IT] Italy ............................... 20672 A/83

[51] Int. Cl.$^4$ ..................... A01N 37/06; A61K 31/22; C11C 1/00
[52] U.S. Cl. .................................. 514/558; 260/398; 260/413
[58] Field of Search ................ 260/398, 413; 424/314, 424/335; 514/558

[56] References Cited

U.S. PATENT DOCUMENTS 2,152,642  4/1939  Harper ........................... 260/398 X

OTHER PUBLICATIONS

Chemical Abstracts 94:186621x (1981).
Chemical Abstracts 71:11257f (1969).
Chemical Abstracts 76:108839p (1972).
Chemical Abstracts 92:34148u (1980).
Chemical Abstracts 82:109869j (1975).
Science 209 825–827 (1980).
Carter et al., Chemotherapy of Cancer, 2nd Ed., John Wiley & Sons, N.Y., pp. 26–42 (1981).

Primary Examiner—Helen M. S. Sneed
Attorney, Agent, or Firm—Bucknam and Archer

[57] ABSTRACT

Organic compounds of selenium are prepared by reaction of metallic selenium with eleostearic acid under warming. Tung oil may be used. The compounds contain between 0.1 and 5% by weight of selenium. Pharmaceutical compositions having antineoplastic activity are prepared, which contain as the active component, the organic compound of selenium. The method of treatment of animals and humans affected by neoplastic conditions is described.

5 Claims, No Drawings

SELENIUM COMPOUNDS HAVING ANTINEOPLASTIC ACTIVITY, PROCESS FOR THE PREPARATION THEREOF AND PHARMACEUTICAL COMPOSITIONS THEREFROM

The present invention relates to new organic compounds of selenium, which exhibit a substantial antineoplastic activity. More specifically, the invention covers compounds prepared by addition of selenium to eleostearic acid. This substance is 9,11,13-octadecatrienoic acid of formula

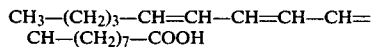

This acid is a fatty acid and is the chief component (about 80%) in "tung oil", also called "china wood oil". According to a preferred method for the preparation of the compounds according to the present invention, "tung oil" is used as a source of eleostearic acid. By warming metallic selenium with eleostearic acid, or more appropriately with "tung oil", at a temperature in the range of 200°-250° C., one notices the disappearance of selenium itself with formation of an addition product in which selenium is bound to the chain of the fatty acid with bonds of various nature (for instance a perselenide, or hydroperselenide, or episelenide bond or others).

The percentage of selenium in the compounds prepared in this manner may vary within a very broad range, for instance between 0.1% up to 5%. However, for the therapeutical use, compounds containing 1–2% by weight of selenium are particularly useful.

The invention also relates to the method of preparation of the novel compounds of the invention which comprises warming selenium with "tung oil" up to the point when the mixture becomes clear, that is when the elementary selenium disappears. The following example illustrates the method of preparation according to the invention without, however, limiting the invention in any way.

EXAMPLE

Selenium, either in the gray or red form, three grams finely powdered, is warmed gradually in 100 grams of tung oil under efficient stirring in a bath of dowtherm. At a temperature of about 230° C., the mixture begins to become clear and becomes completely clear at a temperature of about 248° C. This requires about 2–3 hours of heating. After an additional one half-hour of heating while under efficient stirring, the mixture is allowed to cool and the selenium which has not reacted and which has collected as a single clot, is decanted.

The liquid which is obtained contains 2.03% of selenium, the determination being made by atomic absorption. The ultraviolet spectrum of the compound which will be referred to hereinbelow by the symbol "TSel" exhibits absorption maxima typical of conjugated trienes and conjugated dienes. This fact coupled with the determination of the iodine number, which is carried out with sodium thiosulfate and determining the amount of iodine set free in the reaction between TSel and potassium iodide in acetic acid, shows the presence of selenium bound to carbon atoms adjacent the double bond of a triene in the form of a hydroperselenide group (=C—C—Se—Se—H), and selenium added to a double bond in the form of a perselenide

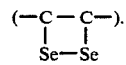

It should be clarified, however, that the novelty of the invention is not in any way limited to the manner of how the selenium is bound in TSel, or more generally, in the compounds according to the present invention.

The substance TSel thus obtained may be administered as such in the form of drops of 50% diluted with sesame oil and administered in unit dosage form in capsules of gelatine or in phthials for injection. The substance in a 2% concentration of selenium prepared as described hereinabove, has been investigated to determine the acute toxicity, subacute toxicity, chronic toxicity and carcinogenic activity. The results are reported hereinbelow.

Acute Toxicity

The acute toxicity of TSel has been tested in mice and rats of both sexes, treated with increasing doses of TSel administered subcutaneously, intraperitoneally and intragastrically.

By the subcutaneous route, no death has been observed when the substance is administered up to 1 cc of TSel in mice (26–32 g ♀ and 28–34 ♂) and up to 2 cc in rats (150–220 g ♀ and 170–230 g ♂). By the intraperitoneal route, the maximum doses which have not caused death, are 0.2 cc for female mice, 0.5 cc for male mice and 0.8 cc for rats of both sexes. The maximum doses which have been tested, 1 cc for mice and 1.5 cc for rats, have caused death in at least 50% of the animals with the exception of female mice which have shown to be more sensitive. The autopsy has shown an atrophization of the suprarenal glands with almost a total disappearance of sudanophilic material.

On the other hand, the administration by the intragastric route of the material up to 1 cc in mice and 2 cc in rats of both sexes has not caused toxic symptoms worth mentioning with the exception of the reduction of the sudanophilic material in the suprarenal glands at the higher dosage.

Subacute Toxicity

Subacute toxicity has been studied by administration of increasing doses of TSel for six consecutive days to mice and rats of both sexes by the subcutaneous route and by the intragastric route and in guinea pigs by the intragastric route.

By the subcutaneous route, only at the highest dose of 0.3 cc, there is observed the death in the treated mice, (1/10 in the female and 2/10 in the male) while no pathological symptoms have been observed in rats treated up to 0.3 cc per 100 grams.

The treatment by the intragastric route has caused no toxic symptoms worth mentioning, with the exception of a slight gastritis at the highest doses in the case of mice (0.3 cc) and rats (0.5 cc). The treatment was, on the other hand, tolerated very well by guinea pigs also at the highest dosage of 0.4 cc.

Chronic Toxicity

Mice weighing 30 grams were subjected to a subcutaneous injection in the amount of 0.1 cc per day, three times a week for a period of three consecutive months.

The animal presented no abnormal reaction with respect to the controls, nor was any pathological change noted in the animals after they had been killed. An equal result was obtained in the rats treated with 0.2 cc per 100 grams. No toxic reaction was observed by administration of TSel to rats and mice by the oral route by means of a catheter in the dose of 1 cc per day for a prolonged period of time and even after adding 1% of TSel to the feed of the same animals.

On the basis of what has been described hereinabove, the compounds according to the invention are practically non-toxic. This is even more surprising if one considers that compounds of selenium are known to be toxic.

Carcinogenic Activity

Thirty male mice of 23-27 grams weight and 30 female mice weighing 28-31 grams were fed for one year a feed in the form of pellets, each one of them contains 0.1 cc of TSel.

At the end of the period of treatment, no case of neoplastic condition was noted.

Pharmacological Properties

The concept of anabolic-catabolic dualism and relative definitions, as described hereinbelow, is amply illustrated also from an experimental point of view, in the case of lower animals by E. Revici, *Research in Physiopathology*, Van Nostrand, Ed., Princeton, 1961.

It should be noted, however, that the invention is not based on the correctness of the theoretical considerations discussed in the work by E. Revici.

The compounds according to the present invention exhibit a marked catabolic effect, as shown by a series of tests. The administration of the substances by the oral route or parenteral route to rats, mice, guinea pigs and rabbits, induces a leukopenia below 6000 per cubic millimeter, with an eosinopenia, the value of which is below 60 per cubic millimeter, corresponding to a catabolic action. In addition, in the lower animals one notes an increase of potassium in the serum with a decrease of the same potassium in eritrocytes, always corresponding to a catabolic action.

The substance TSel and the other compounds according to the present invention cause changes in the urine, which may be summarized as follows: lowering of surface tension to below 66 dynes per centimeter; an increase in specific gravity to a point above 1016; lowering of pH to a point below 6, thus always exhibiting a catabolic action.

By means of analyses of atomic absorption, one notes that selenium is uniformly divided in the organism and is reduced in drastic measure in the period of 48 hours following the administration, selenium itself being transported by the erythrocytes mainly and being eliminated through the feces and urine. If the substance TSel is administered to animals having tumors, the analyses of atomic absorption show that 75% of selenium is fixed on the tumors themselves. In addition, about the same amount of selenium is found again in tumors of animals after they have been killed, one or two weeks after administration.

It has been found by the cytochemical analyses that selenium is present almost exclusively in the cytoplasm of cancerous cells. Histological studies have shown a substantial increase in pyknosis and cellular carrhiorexi of cancerous cells with necrotic zones.

In the study of oxygen absorption by ascitic cells of mice suffering from cancer, and oxygen absorption by yeast, the compounds according to the present invention cause an increase in the absorption itself corresponding to a catabolic action. When administered orally or administered in rats by injection, the compounds according to the present invention, cause a change towards higher pH values in the scab of wounds one day old. Control animals have shown a pH between 7.62 and 7.64, while in other treated animals, the pH reaches 7.80 showing a substantial catabolic action. The study of the effect exerted by the products according to the present invention on the curve of recovery of an epidermic wound in mice and in rats shows also a substantial catabolic action, which is manifested by the substantial increase in peaks and by the prolonged period of recovery.

The oral administration of the compounds according to the present invention, in selected mice of $FC_1$ origin, which in the controls exhibit 45% spontaneous cancer during one year of observation, has shown a reduction of spontaneous cancer to about 8%.

In another group of experiments, the oral administration of TSel for one year, in the dose of 0.2 cc per "pellet" of Purina feed, has been capable of achieving a reduction in the incidence of spontaneous cancer from 40.6% in the controls to 3.3%.

The administration to mice and rats which had undergone a transplant of various tumors has shown a substantial decrease in the percentage of positive results from 100% in the controls to an average of 4% in the treated animals. The administration to animals having transplanted tumors has induced constantly the reduction in growth, and in the case of intramuscular transplant, it has caused the disappearance of tumors administered with compounds to an extent more than 60%.

By way of example, the results obtained in mice in which ascitic cancerous Ehrlich cells had been transplanted, by the intramuscular route are reported hereinbelow.

The animals were treated for six days with an injection of TSel in the dosage indicated hereinbelow.

| Antitumoral Activity of TSel; Mice $CF_1$ | | | |
|---|---|---|---|
| No. of Animals | Sex | Dose | Tumors |
| 10 | ♂ | — | 10/10 |
| 10 | ♀ | — | 10/10 |
| 10 | ♂ | 0.05 cc | 2/10 |
| 10 | ♂ | 0.2 cc | 0/10 |
| 10 | ♀ | 0.1 cc | 0/10 |
| 10 | ♀ | 0.3 cc | 0/10 |

I claim:

1. An organic compound of selenium prepared from eleostearic acid and selenium, which contains 0.1%–5% of selenium, exhibits ultraviolet absorption maxima typical of conjugated trienes and conjugated dienes.

2. The compound according to claim 1 wherein the selenium content is 1–2%.

3. The process of preparing an organic compound of selenium from eleostearic acid and selenium, which consists of reacting 100 parts of eleostearic acid with 3 parts of powdered selenium at a temperature of 200°–250° C. for a period of 2–3 hours, until the reaction product becomes completely clear, continuing heating the reaction product for an additional one-half hour, and decanting off the selenium which has not reacted.

4. A pharmaceutical composition having antineoplastic activity in lower animals which contain as the active component, an organic compound of selenium according to claim 1 in unit dosage form.

5. A method of treatment of lower animals affected by a neoplastic condition which consists of administering 0.25–3 cc of an organic compound according to claim 1, orally or parenterally, 2–4 times daily until disappearance of the neoplastic condition.

* * * * *

UNITED STATES PATENT AND TRADEMARK OFFICE
CERTIFICATE OF CORRECTION

PATENT NO. : 4,564,634
DATED : JANUARY 14, 1986
INVENTOR(S) : EMANUEL REVICI

It is certified that error appears in the above-identified patent and that said Letters Patent are hereby corrected as shown below:

On the title page correct to read as follows:

[73] Assignee;

1] F.C.N. s.r.l
   Treviglio [Italy]

2] ALPHATIME LTD, COMPANY INC.

Signed and Sealed this

Sixth Day of May 1986

[SEAL]

Attest:

DONALD J. QUIGG

Attesting Officer

Commissioner of Patents and Trademarks